US009867872B2

(12) United States Patent
Bruins et al.

(10) Patent No.: US 9,867,872 B2
(45) Date of Patent: *Jan. 16, 2018

(54) USE OF AN ACIDIC SOFT DRINK TO ENHANCE THE EFFICACY OF A GLUTEN-DIGESTING ENZYME

(71) Applicant: DSM IP ASSETS B.V., Heerlen (NL)

(72) Inventors: Maaike Johanna Bruins, Kaiseraugst (CH); Frits Koning, Kaiseraugst (CH); Veronica Montserrat, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/915,973

(22) PCT Filed: Aug. 20, 2014

(86) PCT No.: PCT/EP2014/067717
§ 371 (c)(1),
(2) Date: Mar. 2, 2016

(87) PCT Pub. No.: WO2015/032620
PCT Pub. Date: Mar. 12, 2015

(65) Prior Publication Data
US 2016/0213756 A1    Jul. 28, 2016

(30) Foreign Application Priority Data

Sep. 5, 2013    (EP) .................................... 13183253
Sep. 12, 2013   (EP) .................................... 13184139

(51) Int. Cl.
| | |
|---|---|
| A61K 38/48 | (2006.01) |
| A23L 2/68 | (2006.01) |
| C12N 9/62 | (2006.01) |
| A23L 2/52 | (2006.01) |
| A23L 2/54 | (2006.01) |
| A61K 9/00 | (2006.01) |
| A61K 47/02 | (2006.01) |
| A61K 47/22 | (2006.01) |
| A61K 47/26 | (2006.01) |
| A23L 29/00 | (2016.01) |
| A61K 38/00 | (2006.01) |

(52) U.S. Cl.
CPC .............. *A61K 38/482* (2013.01); *A23L 2/52* (2013.01); *A23L 2/54* (2013.01); *A23L 2/68* (2013.01); *A23L 29/06* (2016.08); *A61K 9/0095* (2013.01); *A61K 47/02* (2013.01); *A61K 47/22* (2013.01); *A61K 47/26* (2013.01); *C12N 9/62* (2013.01); *C12Y 304/21026* (2013.01); *A23V 2002/00* (2013.01); *A61K 38/00* (2013.01)

(58) Field of Classification Search
CPC .............................. G06Q 30/0241; A23L 2/68
See application file for complete search history.

(56) References Cited

U.S. PATENT DOCUMENTS

2009/0304670 A1    12/2009   Edens

FOREIGN PATENT DOCUMENTS

WO    WO 2012/174127    12/2012

OTHER PUBLICATIONS

Pyle et a. Clinical Gastroenterology and Hepatology, 2005, 3:687-694.*
pH of orange juice, pp. 1-2.*
Caputo et al. Enzyme Research, 2010, 1-9.*
Ladas et al. Aliment Pharmacol Ther., 2013, 37:169-173.*
International Search Report for PCT/EP2014/067717 dated Jan. 8, 2015, four pages.
Written Opinion of the ISA for PCT/EP2014/067717 dated Jan. 8, 2015, four pages.
Database FSTA [Online], Prakash et al., "Stability of rebaudioside A under acidic conditions and its degradation products", *International Food Information Service*, vol. 48, No. 1, 2012, one page.

* cited by examiner

*Primary Examiner* — Bin Shen
(74) *Attorney, Agent, or Firm* — Nixon & Vanderhye P.C.

(57) ABSTRACT

This invention relates to the use of an acidic soft drink for improving the efficiency of gluten digestion and more specifically of a gluten-digesting enzyme supplement. Said use allows maintaining or enhancing gastrointestinal comfort in celiac or non-celiac gluten sensitive individuals, or delaying the onset of gastrointestinal discomfort in non-celiac gluten sensitive healthy individuals using a reduced amount of gluten-digesting enzyme. Furthermore, it relates to an acidic soft drink having a pH in the range of 2 to 3.5 for use to support gluten digestion, and to prevent gastrointestinal discomfort following the ingestion of a gluten-containing meal by a gluten-sensitive consumer.

11 Claims, 1 Drawing Sheet

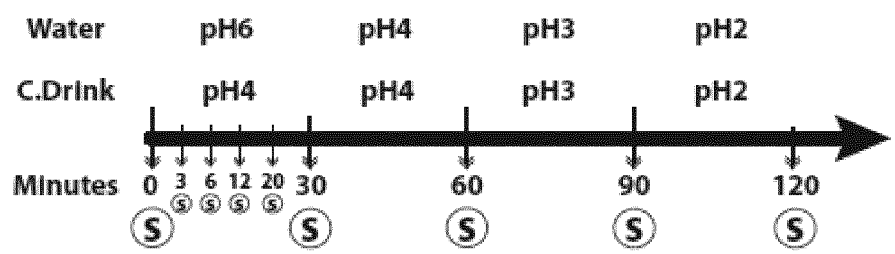
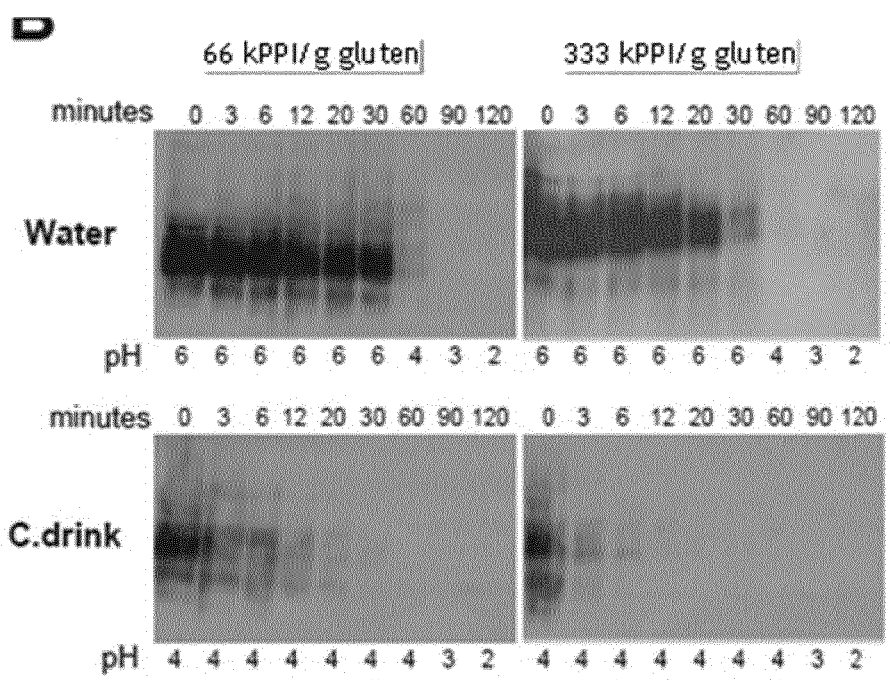

USE OF AN ACIDIC SOFT DRINK TO ENHANCE THE EFFICACY OF A GLUTEN-DIGESTING ENZYME

This application is the U.S. national phase of International Application No. PCT/EP2014/067717 filed 20 Aug. 2014 which designated the U.S. and claims priority to EP Patent Application No. 13183253.7 filed 5 Sep. 2013 and EP 13184139.7 filed 12 Sep. 2013, the entire contents of each of which are hereby incorporated by reference.

BRIEF DESCRIPTION OF THE INVENTION

This invention relates to the use of an acidic soft drink for improving the efficiency of gluten digestion and more specifically of a gluten-digesting enzyme supplement. Said use allows maintaining or enhancing gastrointestinal comfort in celiac or non-celiac gluten sensitive individuals, or delaying the onset of gastrointestinal discomfort in celiac or non-celiac gluten sensitive healthy individuals using a reduced amount of gluten-digesting enzyme. Furthermore, it relates to an acidic soft drink having a pH in the range of 2 to 3.5 for use to support gluten digestion, and to prevent gastrointestinal discomfort following the ingestion of a gluten-containing meal by a gluten-sensitive consumer.

BACKGROUND OF THE INVENTION

Celiac disease, also known as celiac sprue, gluten-sensitive enteropathy, or gluten intolerance is one of the most frequent food intolerances worldwide, with highest prevalence in Europe, North and South America, and Australia. Celiac disease is an inflammatory disease of the upper small intestine in genetically predisposed persons triggered by the ingestion of wheat, barley, rye and their cross-related varieties leading to a mal-absorption syndrome.

Gluten is a common dietary protein present in wheat, barley, rye and their cross-related varieties. Gluten is a complex mixture of glutamine- and proline-rich glutenin and prolamine molecules, which is thought to be the responsible factor for celiac disease induction in sensitive human individuals.

Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac Sprue include fatigue, chronic diarrhea, mal-absorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European and North American populations.

There is some discrepancy about who/when people develop gluten intolerance. Some medical authorities claim there are two peak periods during which onset takes place. The first being infancy, between six months to two years of age, and the second being between the ages of thirty and fifty years. Women are more prone to gluten intolerance than men.

The current essential treatment of gluten intolerance is a permanent strict withdrawal of gluten form the diet. It is however important to define two categories of gluten intolerance in order to understand how the illness is affected by enzyme action in the gut. Celiac sprue is an autoimmune condition, a genetic inflammatory disorder of the small intestine. When gluten proteins break down during digestion, they fragment. These protein fragments are called peptides. In celiac sufferers, an inappropriate immune system response in the small intestine is initiated by one type of peptide, and the intestinal cells are damaged.

A second type of gluten intolerance results when the gut is injured by something other than celiac disease—the negative effect of a bacteria or yeast infection, for example, resulting in the loss of the intestinal enzymes which in turn leads to poor gluten digestion. While supplementing individuals with enzymes may be beneficial to celiac sufferers, they must remain on a strictly gluten free diet because of the possible strength of the reaction.

Using specific enzymes as supplement can be effective in minimizing the need for a gluten-free diet for those individuals at risk of developing gluten intolerance, or wherein gluten intolerance is due to gut injury.

The use of exogenous proteolytic enzymes for gluten detoxification is one of the most promising strategies for celiac disease treatment. Such enzymes have been used in both pretreatment of gluten containing flours, and as supplements. Prolyl-endoproteases are known gluten-digesting enzymes which have been shown to digest gliadin peptides.

WO 02/45524 and WO 02/46381 both disclose a proline specific endoprotease, and the use of said proline specific endoprotease for hydrolyzing proline rich peptides.

WO2013/083338 discloses recently identified specific proteolytic enzymes isolated from an *Actinoallomurus* strain which can be used in food processing to hydrolyze gluten.

However, the kinetics of the above referenced enzymes is not optimal when used as a supplement leading to a need to largely overdose the enzyme ingested by an individual in order to guarantee a timely digestion of the gluten.

It would be desirable to provide a safe an effective way to maintain or enhance gastrointestinal comfort in celiac or non-celiac gluten sensitive individuals, or to delaying the onset of gastrointestinal discomfort in non-celiac gluten sensitive healthy individuals as well to reduce gluten exposure in people desirous of such reduction.

DETAILED DESCRIPTION OF THE INVENTION

It has been found, in accordance with this invention that the efficacy of a gluten-digesting enzyme is stimulated by addition of an acidic soft drink having a pH in a range from 2 to 3.5.

Thus one aspect of this invention is the use of an acidic soft drink having a pH between 2 and 3.5 for improving the efficiency of gluten-digesting enzymes to hydrolyze gluten. In the present invention, the term improving the efficiency means either, reducing the amount of enzyme to obtain identical gluten digestion, or to increase the speed at which a same amount of gluten is degraded.

Said use allows to enhance gastrointestinal comfort in celiac or non-celiac gluten sensitive individuals, or to delay the onset of gastrointestinal discomfort in celiac or non-celiac gluten sensitive healthy individuals, or to reduce gluten exposure in individuals desirous or reducing their gluten exposure.

Definitions

As used throughout the specification and claims, the following definitions apply:

"Gluten-digesting enzyme"—this is an enzyme capable of degrading gluten (complex mixture of glutamine- and proline-rich glutenin and prolamine molecules). It can be any type of endoprotease, but the preferred endoprotease is a prolyl-endopeptidase, and even more preferred is the *Aspegillus niger* prolyl endopeptidase. Prolyl endopeptidase is a large cytosolic enzyme that belongs to a distinct class of serine peptidases. It was first described in the cytosol of rabbit brain as an oligopeptidase, which degrades the nonapeptide bradykinin at the Pro-Phe bond. The enzyme is involved in the maturation and degradation of peptide hormones and neuropeptides such as alpha-melanocyte-stimulating hormone, luteinizing hormone-releasing hormone (LH-RH), thyrotropin-releasing hormone, angiotensin, neurotensin, oxytocin, substance P and vasopressin. PREP cleaves peptide bonds at the C-terminal side of proline residues. Its activity is confined to action on oligopeptides of less than 10 kD and it has an absolute requirement for the trans-configuration of the peptide bond preceding proline. Most preferred prolyl endopeptidase is AN-PEP enzyme. *Aspegillus niger* proline endopeptidase was obtained from DSM Food Specialties (Delft, The Netherlands)).

"Gastrointestinal comfort"—is central to the quality of life. Promoting gastrointestinal digestive comfort includes regulating transit time through the gastrointestinal tract and easing the pain associated with digestion and associated disorders.

"Non-celiac gluten sensitive"—Non-celiac gluten sensitivity has been coined to describe those individuals who cannot tolerate gluten and experience symptoms similar to those with celiac disease but yet who lack the same antibodies and intestinal damage as seen in celiac disease. Non-celiac gluten sensitivity is an innate immune response, as opposed to an adaptive immune response (such as autoimmune) or allergic reaction. Non-celiac gluten sensitivity shares many symptoms with celiac disease. However, according to Sapone et al. (2012), individuals with non-celiac gluten sensitivity have a prevalence of extra intestinal or non-gastrointestinal symptoms, such as headache, "foggy mind," joint pain, and numbness in the legs, arms or fingers. Symptoms typically appear hours or days after gluten has been ingested, a response typical for innate immune conditions like non-celiac gluten sensitivity.

"Healthy individual"—when used in context of this invention, the healthy individual has not been diagnosed as having a celiac disease.

"Delaying the onset" is meant to include amelioration of the condition, lessening of the severity of the symptoms, early intervention, and lengthening the duration of time prior to the onset of the disease, and is not intended to be limited to a situation where the patient is unable to experience any symptoms of gastrointestinal discomfort.

The present invention thus provides the use of an acidic soft drink having a pH between 2 and 3.5 for improving the efficiency of gluten-digesting enzymes to hydrolyze gluten.

In all embodiments of the present invention, gluten-digesting enzymes preferably comprise a prolyl endopeptidase, even more preferred, gluten-digesting enzymes comprise an *Aspergillus niger* prolyl endopeptidase. Moreover, in all embodiments, gluten digesting enzymes are preferably in the form of food supplement. The supplement is preferably in the form of a tablet, a capsule, a sachet, or any other dosage form. More preferably, it is in the form of a tablet or a capsule. The capsules, tablets or sachets or other dosage forms may be in a container which may take any conventional form. For example the dosage forms may be sold in a jar, bottle, tin box, pot, dispenser or the like which contains the dosage forms in a predetermined quantity, such as a 30-day supply, a 60-day supply, a 90-day supply or in whatever quantity which is desired. Additionally and optionally, the capsules may be in a blister pack, wherein each blister contains a predetermined number of capsules, usually a single dose (typically 1-4 capsules). The arrangement of the number of capsules in a blister, the number of blisters on a single blister pack strip, and the number of blister pack strips which are sold in a group may be any convenient amounts or configurations.

In all the embodiments according to the present invention, the acidic soft drink is preferably carbonated, meaning that carbon dioxide gas under pressure has been dissolved in the soft drink. This process, known as carbonation, is a process that causes the drink to become effervescent.

In all the embodiments according to the present invention, the acidic soft drink may further comprise 1 to 500 mili mole per liter of phosphoric acid, preferably, 50 to 300 mmole per liter phosphoric acid. Phosphoric acid (also known as orthophosphoric acid or phosphoric (V) acid) is a mineral (inorganic) acid having the chemical formula $H_3PO_4$. Orthophosphoric acid molecules can combine with themselves to form a variety of compounds which are also referred to as phosphoric acids, but in a more general way. The term phosphoric acid can also refer to a chemical or reagent consisting of phosphoric acids, such as pyrophosphoric acid or triphosphoric acid, but usually orthophosphoric acid.

The conjugate base of phosphoric acid is the dihydrogen phosphate ion, $H2PO^-_4$, which in turn has a conjugate base of hydrogen phosphate, $HPO^{2-}_4$, which has a conjugate base of phosphate, $PO^{3-}_4$.

Furthermore, the acidic soft drink may also comprise 10 to 500 mg/liter caffeine, preferably, 50 to 300 mg/liter, and/or 10 mg/liter to 45 g/liter caramel, and/or 20 to 60 g/liter carbohydrate. Alternatively, in all embodiments of the present invention the acidic soft drink may further comprise one or more artificial sweetener. Sweeteners are preferably selected from stevia, aspartame, sucralose, neotame, acesulfame potassium, and saccharin in replacement of a carbohydrate. Preferred artificial sweetener according to the present invention is from stevia.

In another preferred embodiment, the acidic soft drink further comprises 0.1 to 2 g/serving vitamin C.

In all embodiments of the present invention, the acidic soft drink and the gluten-digesting enzyme are added in a ratio in a range from 3:100 ml/Protease Picomol International units to 3:10,000 ml/Protease Picomol International units. One PPI (Protease Picomole International) is defined as the amount of enzyme that releases one picomole of p-nitroanilide per second at 37° C. in a citrate/disodium phosphate buffer (pH 4.6) using 0.37 mM Z-Gly-Pro-pNA (Bachem, Bubendorf, Switzerland) as substrate.

Alternatively, PPU may also be used. Proline Protease Unit (PPU) is defined as the amount of enzyme that releases 1 μmol of p-nitroanilide per minute at 37° C. in a citrate/disodium phosphate buffer (pH 4.6) using 0.37 mM Z-Gly-Pro-pNA (Bachem, Bubendorf, Switzerland) as substrate. The AN-PEP sample used has a specific activity of 15.7 PPU/g. The conversion factor between PPI and PPU is 1 PPU=16,667 PPI.

When the use according to the present invention is in human, the following conditions are to be adhered to: the acidic soft drink having a pH in the range from 2 to 3.5 needs to be absorbed at the same time, or preferably within 10 minutes from administering the gluten-digesting enzyme supplement, so as to ensure an optimal gluten digestion activity. In such a case, the gluten-digesting enzyme supplement provides from 10,000 to 100,000 Protease Picomole International of gluten-digesting enzyme, wherein the acidic soft drink and the gluten-digesting enzyme are consumed in a ratio of 0.1 L/10,000 Protease Picomole International to 1 L/10,000 Protease Picomole International units.

Formulations

The nutraceutical and pharmaceutical compositions according to the present invention may be in any galenic form that is suitable for administering to humans, but oral forms are preferred, e.g. in solid form, such as additives/supplements for food, tablets, pills, granules, dragées, capsules, gummy formulations, and effervescent formulations such as powders and tablets, or in liquid form such as solutions, emulsions or suspensions as e.g. beverages, pastes and oily suspensions. The pastes may be encapsulated in hard or soft shell capsules, whereby the capsules feature e.g. a matrix of (fish, swine, poultry, cow) gelatin, plant proteins or lignin sulfonate. The dietary and pharmaceutical compositions may be in the form of controlled (delayed) release formulations.

The dietary compositions according to the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, gelling agents, gel forming agents, antioxidants and antimicrobials.

In addition the pharmaceutical or nutraceutical compositions according to the present invention may further contain conventional pharmaceutical additives and adjuvants, excipients or diluents, including, but not limited to, water, gelatin of any origin, vegetable gums, ligninsulfonate, talc, sugars, starch, cellulose, microcrystalline cellulose, gum arabic, vegetable oils, polyalkylene glycols, flavoring agents, preservatives, stabilizers, emulsifying agents, buffers, lubricants, colorants, wetting agents, fillers, and the like. The carrier material can be organic or inorganic inert carrier material suitable for oral/parenteral/injectable administration.

The present invention also provides an acidic soft drink having a pH in the range of 2 to 3.5 as described in all above embodiments for use to support gluten digestion and to prevent gastrointestinal discomfort following the ingestion of a gluten-containing meal by a gluten-sensitive consumer.

In another embodiment, the present invention provides an acidic soft drink having a pH in the range of 2 to 3.5 as described in all above embodiments co-administered with a gluten-digesting enzyme as in all above embodiments, for use to prevent gastrointestinal discomfort following the ingestion of a gluten-containing meal.

Co-administration means administration at the same time or within 10 minutes prior or after absorbing the enzyme supplement.

The following non-limiting Examples are presented to better illustrate the invention.

EXAMPLES

Example 1: Use of an Acidic Soft Drink to Enhance the Efficacy of *A. niger* Prolyl-Endoprotease (AN-PEP)

In Vitro Digestion

Stomach conditions were mimicked in a mixture incorporating 2.2 g of wheat gluten powder (Amygluten 110, Syral, Aalst, Belgium, 77% protein of which 80% gluten), 1 mmol/l $NaHCO_3$, 18 µg/ml pepsin (Pepsin A, from Porcine Stomach Mucosa, 250 units/mg, Sigma, USA) in a total volume of 275 ml. The gluten mixture was incubated with the quantities of *Aspergillus niger* prolyl endopeptidase (AN-PEP) indicated under continuous stirring at 37° C. The pH of the mixture was lowered during the incubation as indicated. Samples of 1 mL were collected at several time points as indicated and immediately stored at −80° C. until further analysis. The soft drink used in the present assay is Coca Cola.

Testing of Various Parameters

The dose-response of AN-PEP on gluten degradation was determined by adding incremental enzyme doses to the incubation mixture. The effect of a carbonated acidic soft drink on gluten degradation was tested by suspending 2.2 g gluten powder in a 1:1 (v/v) mixture of water and carbonated drink to reach a total volume of 275 ml.

A Carbonated Drink Improves AN-PEP Mediated Gluten Degradation

Gluten powder, artificial saliva, pepsin and AN-PEP (either 66,664 or 333,320 PPI/g of gluten) were incubated either in water or in a 1:1 mixture of water and a carbonated drink. Subsequently, both mixtures were incubated, as described in FIG. 1, and the presence of gluten proteins and peptides was determined by Western blot and by ELISA (FIG. 1). The results indicate that gluten degradation in both the soluble and insoluble fraction was significantly faster in the presence of the carbonated acidic soft drink, particularly at the highest enzyme concentration.

FIG. 1: *Aspergillus niger* prolyl endopeptidase (AN-PEP) activity in the presence of an acidic soft drink: A suspension of gluten powder in water was incubated in the presence or absence of an acidic soft drink (Coca Cola) under stomach-like conditions in the presence of either 66,000 PPI (Protease Picomole International) or 333,000 PPI AN-PEP/g gluten. The samples were taken at indicated time points. From the water-insoluble fraction the presence of DQ2.5-glia-α1 epitopes was determined by Western blot as well as from the water-soluble fraction the presence of DQ2.5-glia-α3 was determined by ELISA.

AN-PEP activity in the presence of a carbonated drink. A suspension of 2.2 g gluten powder in water was incubated in the presence of a carbonated drink or water under stomach-like conditions in the presence of either 66,664 or 333,320 PPI AN-PEP/g gluten. The samples were taken at indicated time points. From the water-insoluble fraction the presence of DQ2.5-glia-α1 epitopes was determined by Western blot (upper panel) and from the water-soluble fraction the presence of DQ2.5-glia-α3 was determined by ELISA.

Example 2

A 30 year old gluten sensitive woman took a dietary supplement containing 160,000 PPI AN-PEP with her gluten-free sandwich, and had a 330 mL of Diet Coke with it. She did not experience the gastrointestinal discomfort, as she often does, even after meals which only contain minor amounts of gluten (below 20 ppm).

What is claimed is:

1. A method for improving efficiency of a gluten-digesting enzyme to hydrolyze gluten in a gluten sensitive individual comprising co-administering to a gluten sensitive individual an effective amount of a gluten-digesting enzyme and a carbonated acidic soft drink comprising 1 to 500 mmole per liter of phosphoric acid and having a pH between 2 and 3.5.

2. The method according to claim 1, wherein the gluten-digesting enzyme comprises a prolyl endopeptidase.

3. The method according to claim 1, wherein the gluten-digesting enzyme comprises *Aspergillus niger* prolyl endopeptidase.

4. The method according to claim 1, wherein the gluten-digesting enzyme is in the form of a food supplement.

5. The method according to claim 4, wherein the food supplement is a tablet or a capsule.

6. The method according to claim 1, wherein the acidic soft drink further comprises 10 to 500 mg/liter caffeine.

7. The method according to claim 1, wherein the acidic soft drink further comprises 10 mg/liter to 45 g/liter caramel.

8. The method according to claim 1, wherein the acidic soft drink further comprises 20 to 60 g/liter carbohydrate.

9. The method according to claim 1, wherein the acidic soft drink further comprises one or more artificial sweetener.

10. The method according to claim 1, wherein the acidic soft drink further comprises 0.1 to 2 g/serving vitamin C.

11. The method according to claim 1, which comprises co-administering the acidic soft drink and the gluten-digesting enzyme in a ratio in a range from 3:100 ml/Protease Picomol International units to 3:10,000 ml/Protease Picomol International units.

* * * * *